United States Patent [19]
Trifonov et al.

[11] Patent Number: 5,948,442
[45] Date of Patent: Sep. 7, 1999

[54] STIMULATING ENTEROGENIN COMPOSITIONS AND METHODS FOR THEIR ISOLATION AND USE

[75] Inventors: Borislav Borisov Trifonov; Jeorge Konstantinov Roussev; Nikola Atanassov Boshev; Metodi Stefanov Petrov, all of Plovdiv, Bulgaria

[73] Assignee: Christo Alexandrov Alexandrov, Bulgaria

[21] Appl. No.: 08/809,761

[22] PCT Filed: Oct. 9, 1995

[86] PCT No.: PCT/BG95/00009

§ 371 Date: Mar. 17, 1997

§ 102(e) Date: Mar. 17, 1997

[87] PCT Pub. No.: WO97/03653

PCT Pub. Date: Feb. 6, 1997

[30] Foreign Application Priority Data

Jul. 19, 1995 [BG] Bulgaria .................................. 99795

[51] Int. Cl.$^6$ .......................... A61K 35/37; A61K 35/38; A01N 63/00; A01N 65/00
[52] U.S. Cl. .......................... 424/551; 424/550; 424/937
[58] Field of Search .................................. 424/93.7, 551, 424/550

[56] References Cited

FOREIGN PATENT DOCUMENTS

BG 37396  6/1985  Norway .
BG 49927  3/1992  Norway .

OTHER PUBLICATIONS

Skraastad O, Reichelt KI, Virchows Arch B, 56, 1989, 393–396.

Skraastad O, Reichelt KI, J Gastroent 23, 1986, 801–807.

Triffnov B, et al., Regulatory Peptides, 51, 1994, 111–119.

Triffonov B, et al, J Gastrointest Motil 4, 1992, 193–199.

Popov, et al, 1986, "The Effect of a Stimulatory Enterocytogenin . . . " Folia Media, pp. 28–31.

Trifonov, et al, 1994, "Biological Effects of a Novel Peptide . . . " Regulatory Peptide 51:111–119.

*Primary Examiner*—Lynette R. F. Smith
*Assistant Examiner*—Brett Nelson
*Attorney, Agent, or Firm*—Fitch, Even, Tabin & Flannery

[57] ABSTRACT

This patent relates to the obtaining of two pharmaceutical forms—pulvis and ampules of the veterinary medical preparation "Enterogenin". The bioactive ingredient of the preparation is isolated by fractionation of pig small intestinal mucosa cell, extraction with acetic acid, sedimentation with ethyl alcohol, ion-exchange chromatography and diaflo ultrafiltration in the range of 0.5–2 kDa. The bioactivity of the preparation is related to two nucleopeptides: guanosine tripeptide and adenosine heptapeptide. The basic criterion for the biological action of "Enterogenin" pulvis and ampules is the activation of biosynthesis of nucleic acids and specific proteins in the muscles, liver, intestines and spleen.

15 Claims, 1 Drawing Sheet

STIMULATING ENTEROGENIN COMPOSITIONS AND METHODS FOR THEIR ISOLATION AND USE

This is a 371 of PCT/BG95/00009 filed Oct. 9,1995.

BACKGROUND OF THE INVENTION

The invention relates to the preparation "ENTEROGENIN—pulvis and ampules", the method for its isolation on an industrial scale production of the pharmaceutical forms and investigation of the pharmacological effects of the preparation. The active component of "ENTEROGENIN—pulvis and ampules" is a bioactive substance isolated from intestinal mucosa. Data have been reported about substances present in the intestinal mucosa that inhibit cell proliferation (1,2,3). There are no reports in the literature concerning isolation of substances that exert stimulating effect on morphogenesis. We have patented a method for isolation of biostimulating substance from intestinal mucosa of warm-blooded animals (4,5). This method has certain disadvantages—complex technologic process which renders relatively expensive the production of the substance, and incompleteness of the method to the stage of producing final pharmacologically tested forms.

SUMMARY OF THE INVENTION

This invention has as its objects to: 1) refine the said method for isolation of the bioactive component of the preparation "ENTEROGENIN—pulvis and ampules"; 2) develop pharmaceutical forms of the preparation "ENTEROGENIN—pulvis and ampules"; 3) Test the pharmacological action of the preparation "ENTEROGENIN—pulvis and ampules" in the veterinary and zootechnical practice after experimental investigation of the effects of the bioactive component.

DETAILED DESCRIPTION OF THE INVENTION

Figure 1:
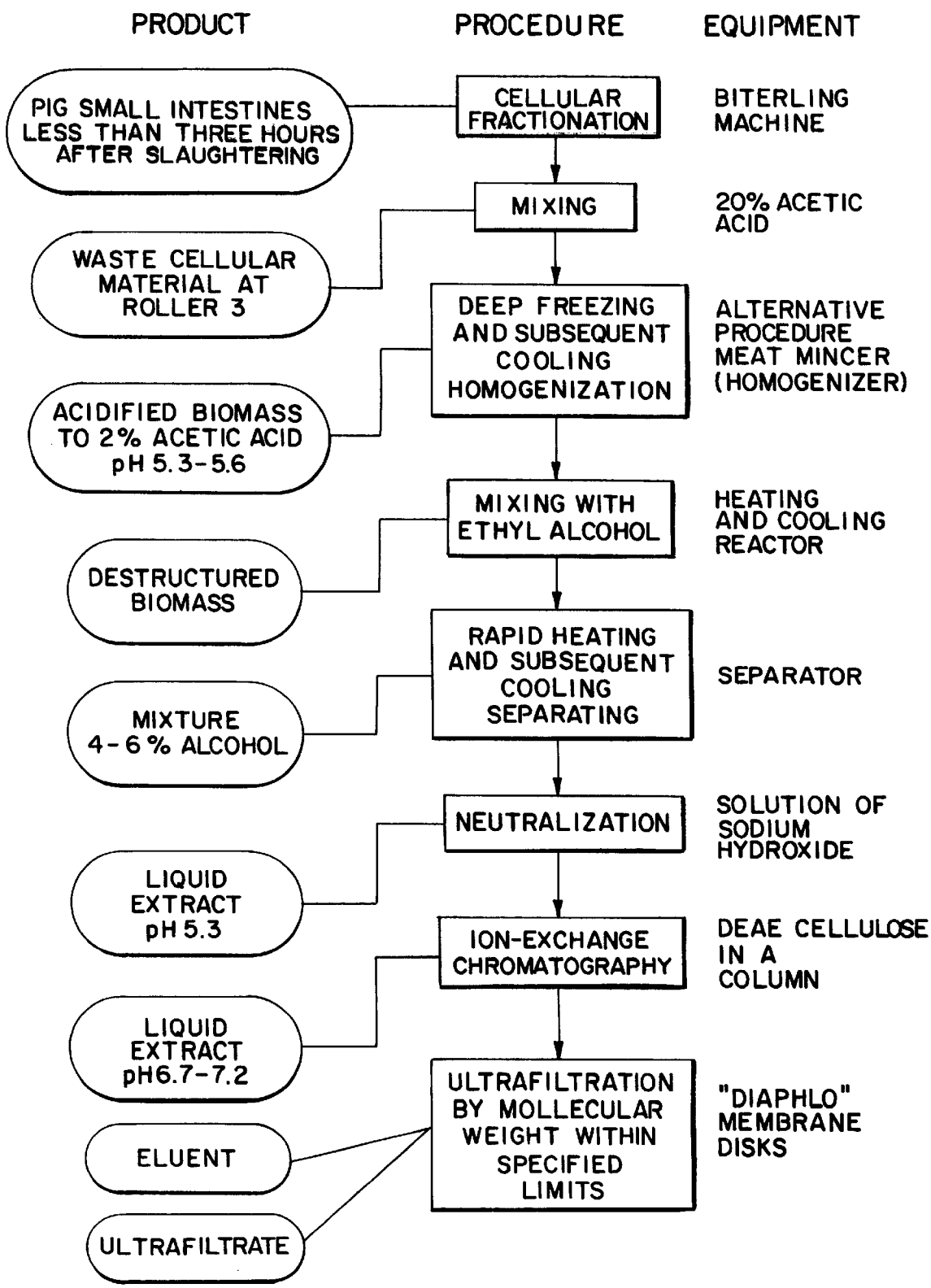
FIG. 1 is a flowchart describing the isolation of stimulating enterogenin.

The first object is accomplished by method for isolation of a stimulator of biosynthetic processes from pig intestinal mucosa. Principally, the production scheme comprises the following steps: 1) isolation of a specific cellular mass from animal intestinal mucosa which is discarded as a waste product in the casing cleaning shops of meat packing plants; 2) obtaining an alcoholic acid extract after settling the high molecular weight polymers; at this stage any contamination associated with the initial biomass is prevented; 3) ion-exchange fractionation in batch procedures; 4) ultrafiltration of the eluent obtained from the fractionation. The technological scheme is described in Example 1.1. Compared with the method described in Patent BG 49927 MPK A61K37/02 the improvements are as follows: the reagents are used in smaller amounts; some of the stages of the basic technologic scheme are changed and their number reduced; the parameters of the ultrafiltration are changed and further specified. As a result, two instead of one bioactive nucleopeptides named by us "stimulating enterocytogenins", have been isolated.

The second object is achieved by preparation of two pharmaceutical forms: 1) packets of enterosolvent granules "ENTEROGENIN pulvis" for peroral administration; 2) vials of "ENTEROGENIN ampules" containing the purified bioactive preparation in a depot form. Stored at a temperature of 2 to 6° C. the pharmaceutical forms can preserve their action for three years. The analysis of the above mentioned pharmaceutical forms has been officially approved by the Laboratory for Veterinary Preparation Control with the National Office of Veterinary Medicine (6). The analysis comprises the reactions for chemical and biological identification of the biologically active nucleopeptides in "ENTEROGENIN". Additionally, an analysis of the vehicle components of the pharmaceutical forms are given.

The third object is achieved by laboratory and clinical experiments and introductions in veterinary practice. The bioactive nucleopeptides contained in "Enterogenin—pulvis and ampules" act at a molecular level; the proliferative cycle of the physiologically regenerating intestinal mucosa cells is shortened which results in an increase of the resorptive surface of small intestines; in non-proliferating cells they stimulate the synthesis of specific proteins: actomyosin in the striated muscles, detoxicating proteins in the liver, immunogenic proteins in the spleen, and digestive enzymes in the gastrointestinal tract. In smooth muscle cells these nucleopeptides induce depolarization by stimulating the $Ca^{2+}$-influx (7).

In small experimental animals the daily use of the preparation increases their body mass by more than 200% Application of "ENTEROGENIN" for 20 days in pig and cattle breeding farms gives as a result a long-term stimulating effect followed up for six months. The effect manifests itself in an increase of the daily weight growth by 125 g for pigs, and by 110 g for calves. In chickens, applied in the drinking water from day 3 to day 45 after hatching, "ENTEROGENIN" stimulates the biosynthesis of DNA and proteins increasing their body weight by 118%. "ENTEROGENIN" has also shown a therapeutic effect in animal models: in experimental stomach ulcers, after liver intoxication, in the prophylaxis of infectious diseases by stimulating the immunogenesis. "ENTEROGENIN" is neither toxic, teratogenic, embryotoxic, nor genotoxic which was proved by tests in the National Oncologic Center and the National Institute of Drug Administration.

The invention will now be described by way of the following examples:

EXAMPLE 1

Task 1

(FIG. 1) On Biterling machine in the casing cleaning wards of the slaughter house the cellular enriched mass removed at casing stripping roller No 3 is collected and 20% cold acetic acid is added simultaneously, at constant stirring, to achieve final concentration of 2% acetic acid relative to the total volume. The processing of the biomass can either proceed further or the biomass can be stored in a freezer cooled to −40° C. If the latter action is opted for partial defrosting is required subsequently. Processing with a meat mincer follows. 95% ethyl alcohol (0.2 volumes of the total mass) is added to the minced material. Then the biomass is rapidly heated to 70° C. and cooled immediately to room temperature. The liquid extract is removed by separation and filtration. The high molecular weight detritus is thrown away. The acidic pH is adjusted to pH 6.5–7.0. The alcohol and the lipid admixtures are removed in ether in a glass reactor. At a constant control of the salt concentration the concentrate is absorbed on DEAE cellulose and eluted by batch procedures using alkalized saline solution. The active fraction is purified through diaflo ultrafilters collecting the fraction in the range of 0.5–2.0 kDa. The second filtration is realised under sterile conditions. The concentration of nucleopeptides is measured which is necessary for the determination of the dosage of the pharmaceutical forms.

EXAMPLE 1

Task 2

The actual preparation of the pharmaceutical forms "ENTEROGENIN—pulvis and ampules" is preceded by chemical and biological investigations designed to identify the nucleopeptides: a) ultraviolet absorption spectrum—max. 260 nm, min. 237 nm; $A_{260}/A_{237} = 1.21–1.19$; b) specific reaction for peptides—e.g. ninhydrin reaction of Reichelt; c) molecular weight determination: by means of Sephadex G-25 fine column precalibrated with peptides with a known molecular weight; by $K_{av}$, the referent limits of the two active nucleopeptides are 1.1–1.3 kDa and 0.6–0.65 kDa, respectively; d) amino acid composition: by "finger print" analysis on paper chromatography or, more exactly, through quantitative determination on amino acid analyzer. Glycine and tryptophan are detected in the low molecular weight nucleopeptide; the other nucleopeptide contains arginine, serine, leucine, histidine, glycine and tyrosine; e) quantitative analysis: spectrophotometric determination of $A_{260}$ against a standard 0.01 mmol adenine sulfate; calculations:

$$\text{Nucleopeptides \%} = \frac{A_{260} \text{ sample}}{A_{260} \text{ standard}} 0.0125$$

f) the biologic activity is determined by measuring the incorporation of $^3$H-leucine (injected intraperitoneally in a dose of 0.04 MBq per 20 g of mouse weight). Eighteen hours after introduction of an isotope (for the control group) and the isotope together with 0.02 mg of "ENTEROGENIN" (for the experimental group) the incorporation of the isotope is measured in 50 mg of muscle tissue taken from the adductors of a rear leg of a mouse.

EXAMPLE 1

Task 3

A rapid criterion for biologic activity of the preparation "ENTEROGENIN pulvis and ampules" is the investigation of the biosynthesis of DNA, RNA and proteins by the incorporation of the corresponding isotropically marked precursors. The mean activation is greater than 200% (Table 1). Long-term morphological changes occur in the animals repeatedly treated with "ENTEROGENIN" (Table 2). The resorptive surface of the intestines expands which increases the effectiveness of the food 2.56-fold at less amount of food taken and raises the coefficient of protein effectivity—2.5 times that of the controls. Morphological changes also occur in the striated muscles—contractile muscle proteins incease relatively. The growth dynamics in calves improved by injecting them 6 times with the preparation, in pigs and fresh water fish by mixing the preparation daily for 20 days in the food, and in chickens by adding the preparation for 45 days in the drinking water.

A pronounced therapeutic effect of "ENTEROGENIN" in two models of experimental ulcers (reserpin and stress-histamin models) in rats has been obtained. After tetrachlormethane intoxication in rats we investigated the dynamics of the metabolic and recuperating processes in the hepatorenal syndrome. The preparation "ENTEROGENIN" showed protective and reparative effects.

TABLE 1

Effect of "ENTEROGENIN" on the biosynthesis of DNA (incorporation of $^3$H-thymidinen), RNA (incorporation of $^{14}$C-uridine), and proteins (incorporation of $^3$H-leucine) [given in percent in relation to the control animals without "Enterogenin"]

| Animal | Body organ | Incorporation | | |
|---|---|---|---|---|
| | | Thymidinen | Uridine | Leucine |
| Rats | Duodenum | 221 | | |
| | Jejunum | 190 | | |
| | Middle part of small intestines | 284 | | |
| | Ileum | 337 | | |
| | Hepatocyte nuclei | 161 | | |
| Mice | Duodenum | 163 | | |
| | Jejunum | 302 | 360 | |
| | Middle part of small intestines | 212 | | 212 |
| | Ileum | 153 | 160 | |
| | Muscle | | | 177 |
| Chickens | White muscle | 103 | | 104 |
| | Middle part of small intestine | 242 | | 265 |
| | Red muscle | 118 | | 193 |
| | Liver | 183 | | 331 |

TABLE 2

Morphologic changes after multiple treatment with "ENTEROGENIN". [given in percent in relation to the control animals without "ENTEROGENIN"]

| Parameter | Body organ | Animal | % of changes |
|---|---|---|---|
| Body weight (g) | Total body weight | mice | 212 |
| | Liver | rats | 159 |
| | Small intestines | rats | 126 |
| | Heart | rats | 135 |
| | Spleen | rats | 112 |
| | Kidney | rats | 120 |
| Cellularity ($\times 10^5$/l/1 $\mu$m$^2$) | Duodenum | rats | 144 |
| | Jejunum | rats | 173 |
| Intestinal mucosa | Middle part of small intestines | rats | 167 |
| | Ileum | rats | 135 |
| | Duodenum | mice | 134 |
| | Jejunum | mice | 163 |
| | Middle part of small intestines | mice | 173 |
| | Ileum | mice | 139 |
| Number of intestinal villi (on microscopic cut) | Middle part of small intestines | mice | 133 |
| Length of an intestinal villus (on microscopic cut/$\mu$m) | Middle part of small intestines | mice | 125 |
| Area of a single muscle fibre ($\mu$m$^2$) | Musculus gastrocnemius | pigs | 191 |
| | Diaphragm | pigs | 279 |
| | Musculus obliquus | pigs | 252 |
| Diameter of a single muscle fibre ($\mu$m in electron microscopy) | Musculus gastrocnemius | pigs | 154 |
| | Diaphragm | pigs | 170 |
| | Musculus obliquus | pigs | 157 |
| Thickness of the Z line ($\mu$m. electron microscopy) | Musculus gastrocnemius | pigs | 300 |

References

1. Skraastad O, Reichelt KI. An endogenous colon mitosis inhibitor reduces proliferation of colon carcinoma cells (HT 29) in serum restricted medium. Virchows Arch B, 50, (1989), 393–390.

2. Skraastad O, Reichelt KI. An endogenous colon mitosis inhibitor and dietary calcium inhibit the increased colonic cells proliferation induced by cholic acid. J Gastroent 23 (1986), 801–807.
3. Triffonov B, Roussev GK, Argirov C, Draganov M, Kamberov B. Biological effects of a novel intestinal peptide—inhibiting enterocytogenin on cultured 3T3 mouse fibroblasts and L5178Y mouse lymphoma cells. Regulatory Peptides, 51 (1994), 111–119.
4. Triffonov B, Roussev GK, Boshev H, Tyanev G. A method for isolation of a biostimulating substance. Patent 49927, BG 49927 MPK A61K37/02, Vol 3, Mar. 16, 1992, 1–3 (Bulgarian).
5. Roussev GK, Triffonov B, Petrov M, Boshev H. A method for isolation of substances with morphogenic activity. Invention patent 37396 MPK-A61K35/38, Vol 6, Jun. 14, 1985, 1–6.
6. Certificate No XIII-33/10.02.1995, Ministry of Agriculture, National Veterinary Office for Licence for production and use of preparation "ENTEROGENIN" in the veterinary practice.
7. Triffonov B, Kristev A, Zaprianov G, Lukanov J, Kostadinova I. Effects of a novel intestinal peptide (enterogenin) on the contractile and bioelectric activity of intestinal smooth muscle from the rat and the guinea-pig. J Gastrointest Motil 4, (1992), 193–199.

We claim:

1. A composition effective for stimulating biosynthetic processes, the composition comprising stimulating enterogenins effective for increasing body weight, the stimulating enterogenins isolated by a method comprising:

isolating cellular biomass from animal intestinal mucosa;

acidifying the cellular biomass and extracting the acidified cellular biomass with alcohol;

separating the alcohol from the cellular biomass;

extracting the alcohol with ether;

fractionating the ether with ion-exchange chromatography to obtain an eluent containing stimulating enterogenins; and purifying the eluent with ultrafiltration and recovering a fraction with a molecular weight of 0.5 to 2.0 KDa, where the stimulating enterogenins comprise a low molecular weight stimulating enterocytogenin having a molecular weight of from about 0.6 to about 0.65 kDa, the low molecular weight stimulating enterogenin further comprising a nucleoside and a peptide chain of glycine and tryptophan, and a high molecular weight stimulating enterogenin having a molecular weight of from about 1.1 to about 1.3 kDa, the high molecular weight stimulating enterogenin further comprising a nucleoside and a peptide chain of arginine, serine, leucine, histidine, glycine and tyrosine.

2. The composition of claim 1, wherein the stimulating enterogenins are in a physiological solution, the physiological solution comprising about 0.0125% stimulating enterogenins and about 0.2% sodium alginate.

3. The composition of claim 1, wherein the stimulating enterogenins are sorbed on starch to provide a starch composition with about 0.125% stimulating enterogenins.

4. A method for isolating stimulating enterogenins, the method comprising:

isolating cellular biomass from animal intestinal mucosa;

acidifying the cellular biomass and extracting the acidified cellular biomass with alcohol;

separating the alcohol from the cellular biomass;

extracting the alcohol with ether;

fractionating the ether with ion-exchange chromatography to obtain an eluent containing stimulating enterogenins; and purifying the eluent with ultrafiltration and recovering a fraction with a molecular weight of 0.5 to 2.0 KDa, where the stimulating enterogenins comprise a low molecular weight stimulating enterogenin having a molecular weight of from about 0.6 to about 0.65 kDa, the low molecular weight nucleopeptide further comprising a nucleoside and a peptide chain of glycine and tryptophan, and a high molecular weight stimulating enterogenin having a molecular weight of from about 1.1 to about 1.3 kDa, the high molecular weight nucleopeptide further comprising a nucleoside and a peptide chain of arginine, serine, leucine, histidine, glycine and tyrosine.

5. A method for stimulating biosynthetic processes, the method comprising administering an amount of stimulating enterogenins effective for increasing body weight, wherein the stimulating enterogenins comprise a low molecular weight stimulating enterogenin having a molecular weight of from about 0.6 to about 0.65 kDa, the low molecular weight stimulating enterogenin further comprising a nucleoside and a peptide chain of glycine and tryptophan, and a high molecular weight stimulating enterogenin having a molecular weight of from about 1.1 to about 1.3 kDa, the high molecular weight nucleopeptide further comprising a nucleoside and a peptide chain of arginine, serine, leucine, histidine, glycine and tyrosine.

6. The method of claim 5 wherein the stimulating enterogenins are sorbed on starch in an amount effective for providing a starch composition with about 0.125% stimulating enterogenins.

7. The method of claim 5 wherein the stimulating enterogenins are in a physiological solution comprising about 0.0125% stimulating enterogenins and about 0.2% sodium alginate.

8. The method of claim 6 wherein the stimulating enterogenins sorbed on starch are administered daily in a forage food of pigs for about 20 to about 30 days at a dosage of about 100 grams of starch composition per about 200 kg of body weight.

9. The method of claim 7 wherein the physiological solution containing the stimulating enterogenins is administered about 6 to about 8 times intramuscularly in ruminants every third day at a dosage of about 0.5 ml of the physiological solution containing the stimulating enterogenins per about 100 kg of body weight.

10. The method of claim 7 wherein the physiological solution containing the stimulating enterogenins is administered daily in drinking water to chickens for about 45 days at a dosage rate of about 0.5 ml of the physiological solution containing the stimulating enterogenins per about 10 kg of body weight.

11. The method of claim 6 wherein the stimulating enterogenins absorbed on starch are administered in a forage food during a breeding period of fresh water fish at a dosage of about 100 grams of starch composition per about 5 kg of forage food.

12. The method of claim 5 wherein the stimulating enterogenins are isolated by a method comprising:

isolating cellular biomass from animal intestinal mucosa;

acidifying the cellular biomass and extracting the acidified cellular biomass with alcohol;

separating the alcohol from the cellular biomass;

extracting the alcohol with ether;

fractionating the ether with ion-exchange chromatography to obtain an eluent containing stimulating enterogenins; and purifying the eluent with ultrafiltration and recovering a fraction with a molecular weight of 0.5 to 2.0 KDa.

13. A composition effective for stimulating biosynthetic processes, the composition comprising stimulating enterogenins effective for increasing body weight, wherein the stimulating enterogenins comprise a low molecular weight stimulating enterogenin having a molecular weight of from about 0.6 to about 0.65 kDa, the low molecular weight stimulating enterogenin further comprising a nucleoside and a peptide chain of glycine and tryptophan, and a high molecular weight stimulating enterogenin having a molecular weight of from about 1.1 to about 1.3 kDa, the high molecular weight stimulating enterogenin further comprising a nucleoside and a peptide chain of arginine, serine, leucine, histidine, glycine and tyrosine.

14. The composition of claim 13, wherein the stimulating enterogenins are in a physiological solution, the physiological solution comprising about 0.0125% stimulating enterogenins and about 0.2% sodium alginate.

15. The composition of claim 13, wherein the stimulating enterogenins are sorbed on starch to provide a starch composition with about 0.125% stimulating enterogenins.

* * * * *